(12) United States Patent
Shock et al.

(10) Patent No.: US 8,555,733 B2
(45) Date of Patent: Oct. 15, 2013

(54) SYSTEM AND METHOD FOR ANALYZING A REFRIGERANT SAMPLE

(75) Inventors: Robert Frances Shock, Cheshire, CT (US); James Gruenbacher, Southington, CT (US); Maciej Kuchcinski, Plainville, CT (US); Alexey Virovets, Sandy Hook, CT (US)

(73) Assignee: Airgas, Inc., Cheshire, CT (US)

( * ) Notice: Subject to any disclaimer, the term of this patent is extended or adjusted under 35 U.S.C. 154(b) by 182 days.

(21) Appl. No.: 13/242,485

(22) Filed: Sep. 23, 2011

(65) Prior Publication Data

US 2013/0074611 A1 Mar. 28, 2013

(51) Int. Cl.
*G01N 1/22* (2006.01)
(52) U.S. Cl.
USPC ........... 73/863.11; 73/863; 137/334; 137/341
(58) Field of Classification Search
USPC ........ 73/863.11, 863.12, 863; 95/73, 90, 273; 137/341, 334
See application file for complete search history.

(56) References Cited

U.S. PATENT DOCUMENTS

| | | | | |
|---|---|---|---|---|
| 4,342,234 | A | * | 8/1982 | Bernath ..................... 73/863.12 |
| 2004/0250855 | A1 | * | 12/2004 | Hyde et al. ..................... 137/341 |
| 2010/0180960 | A1 | * | 7/2010 | Patterson et al. ............. 137/340 |
| 2012/0017669 | A1 | * | 1/2012 | Thompson et al. .......... 73/61.59 |

* cited by examiner

*Primary Examiner* — Hezron E Williams
*Assistant Examiner* — Alexander Mercado
(74) *Attorney, Agent, or Firm* — RatnerPrestia

(57) ABSTRACT

A system for preparing a refrigerant sample for analysis including a pressure regulator assembly including a pressure regulator and provisions for heating a refrigerant sample contained within an interior region of the pressure regulator. The pressure regulator defines an inlet through which the refrigerant sample is delivered and an outlet through which the refrigerant sample is expelled. The system also includes a filter assembly having an inlet that is fluidly connected to the outlet of the pressure regulator to receive the vaporized refrigerant sample from the pressure regulator, at least one filter for removing contaminants from the refrigerant sample, and an outlet that is configured to be coupled to a refrigerant analysis system for analyzing a composition of the refrigerant sample.

9 Claims, 3 Drawing Sheets

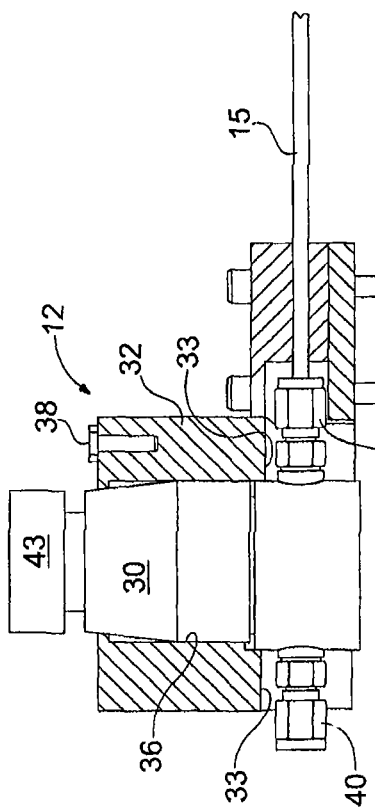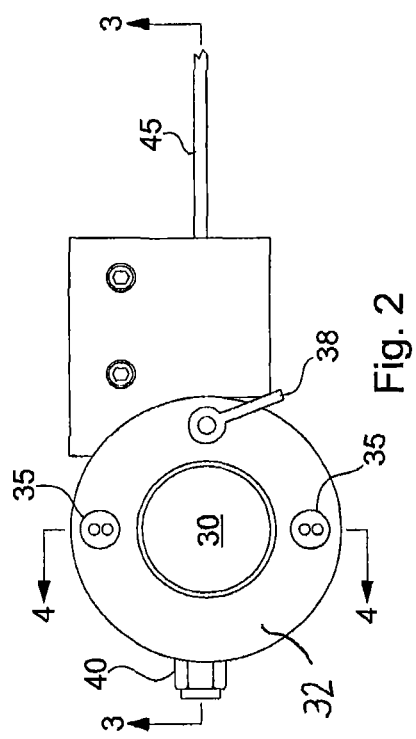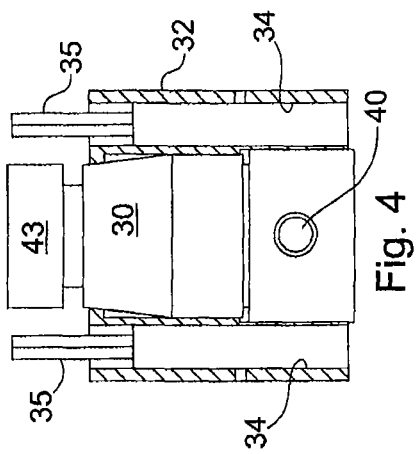

SYSTEM AND METHOD FOR ANALYZING A REFRIGERANT SAMPLE

FIELD OF THE INVENTION

The disclosed invention relates to a system and method for preparing a refrigerant sample for analysis.

BACKGROUND OF THE INVENTION

A key element of the responsible use and stewardship of refrigerants is the recovery, recycling and reclamation of used refrigerants so that they can be reprocessed for further commercial use or destroyed. It has become standard practice in the refrigeration system service industry to recover and reclaim refrigerant for later reuse, rather than merely to vent such refrigerant into the atmosphere, as had been common practice in the past. Refrigerants can be recovered, recycled and reclaimed from many systems, such as mobile air conditioners, stationary air conditioners and refrigeration systems, for example. The recovered refrigerant is then transported to a facility for reclamation.

The reclamation process typically encompasses an initial chemical analysis of a sample of the recovered refrigerant in an effort to identify the composition of the recovered refrigerant that is to be reclaimed. The following steps are commonly performed to prepare the refrigerant sample for analysis: (1) drawing a sample of liquid refrigerant, (2) injecting the sample into a sample bomb, (3) vaporizing the sample in the bomb, (4) filtering the vaporized sample to remove contaminants, such as lubricants, water and metallic particles, and (5) manually introducing the filtered sample into an analytical instrument for analysis, such as mass spectroscopy and gas chromatography. Contaminants, such as oil or other lubricants are filtered from the vaporized sample in step 4 because those contaminants could impair the chromatography process.

The foregoing preparation steps are time consuming, typically consuming 90 minutes or more, and, for that reason, only a small fraction of recovered refrigerant may be analyzed. In order to comply with ever-increasing regulatory demands it has become necessary to conduct a more comprehensive analysis of the recovered refrigerant that is to be reclaimed. Such regulatory demands are defined in Air-conditioning, Heating and Refrigeration Institute (AHRI) Standard No. 700-2006. Thus, there is a need in the industry for a refrigerant sample preparation system that can be employed to more rapidly prepare recovered refrigerant for analysis.

SUMMARY OF THE INVENTION

According to an aspect of the invention, a system for preparing a refrigerant sample for analysis is provided. The system comprises a pressure regulator assembly including a pressure regulator and means for heating a refrigerant sample contained within an interior region of the pressure regulator. The pressure regulator defines an inlet through which the refrigerant sample is delivered and an outlet through which the refrigerant sample is expelled. The system further comprises a filter assembly having an inlet that is fluidly connected to the outlet of the pressure regulator to receive the vaporized refrigerant sample from the pressure regulator, at least one filter for removing contaminants from the refrigerant sample, and an outlet that is configured to be coupled to a refrigerant analysis system for analyzing a composition of the refrigerant sample.

According to another aspect of the invention, a method for preparing a refrigerant sample for analysis is provided. The method includes the step of introducing a refrigerant sample through an inlet of a pressure regulator and into an interior region of the pressure regulator. The refrigerant sample within the interior region of the pressure regulator is heated to vaporize the refrigerant sample. The vaporized refrigerant sample is distributed through a filter to remove contaminants in the refrigerant sample.

BRIEF DESCRIPTION OF THE DRAWINGS

The invention is best understood from the following detailed description when read in connection with the accompanying drawing. Included in the drawing are the following figures:

FIG. 2 is a top plan view of a heated pressure regulator of the system of FIG. 1;

FIG. 3 is a cross-sectional view of the heated pressure regulator of FIG. 2 taken along the lines 3-3;

FIG. 4 is a cross-sectional view of the heated pressure regulator of FIG. 2 taken along the lines 4-4.

DETAILED DESCRIPTION OF THE INVENTION

The invention is best understood from the following detailed description when read in connection with the accompanying drawing, which shows exemplary embodiments of the invention selected for illustrative purposes. The invention will be illustrated with reference to the figures. Such figures are intended to be illustrative rather than limiting and are included herewith to facilitate the explanation of the present invention. In the various embodiments like item numbers represent substantially similar features.

Figure 1:
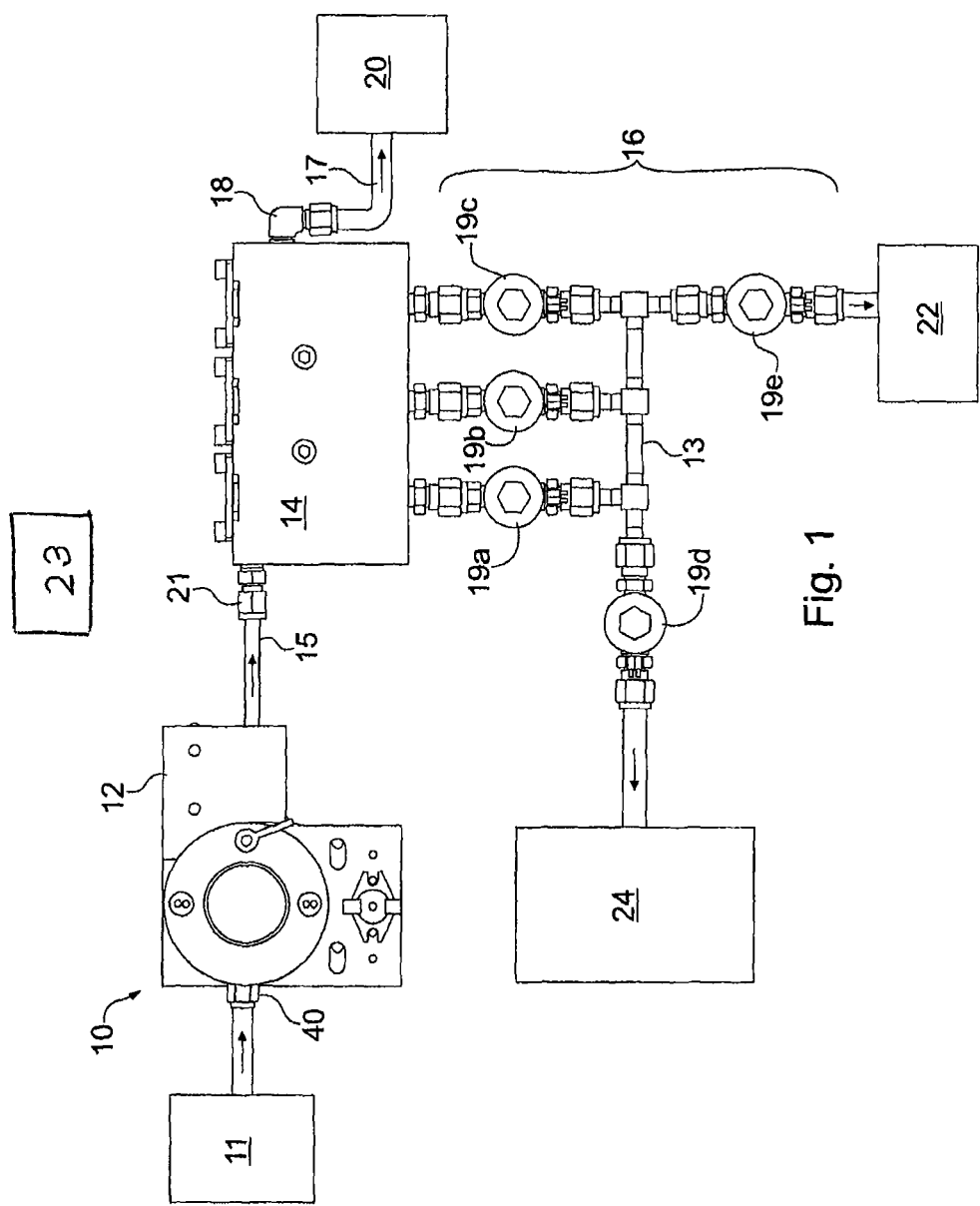
FIG. 1 is a schematic view of refrigerant sample preparation system according to one exemplary embodiment of the invention.

FIG. 1 is a schematic view of refrigerant sample preparation system according to one exemplary embodiment of the invention. The refrigerant sample preparation system, which may be referred to hereinafter as a system, is denoted by the numeral '10.' According to one exemplary embodiment of the invention, the system 10 generally includes a sample container 11 filled with a refrigerant sample, a heated pressure regulator assembly 12 that is fluidly coupled to sample container 11 for heating a refrigerant sample, a filter assembly 14 having an inlet port 21 that is fluidly coupled to pressure regulator assembly 12 via conduit 15 for filtering the heated refrigerant sample, and a conduit system 16 that is fluidly coupled to filter assembly 14 to provide a passageway for venting and vacuuming of system 10. A conduit 17 is fluidly coupled between an outlet port 18 of filter assembly 14 and an analytical instrument 20. The analytical instrument 20 may be a mass spectrometer, a gas chromatograph, or a flame ionization detector, for example. According to one aspect of the invention, analytical instrument 20 is a mass spectrometer and a gas chromatograph.

The conduit system 16 comprises a series of interconnected fluid-carrying pipes 13 and discrete valves 19a-19e mounted to fluid-carrying pipes 13. The conduit system 16 is fluidly coupled to a vacuum source 22, which is configured to evacuate filter assembly 14 and pressure regulator assembly 12. The conduit system 16 is also fluidly coupled to a venting container 24 for collecting refrigerant sample that is utilized for flushing filter assembly 14 and regulator assembly 12. The venting container 24 may be a refrigerant reclamation system, for example. A series of discrete valves 19a-19e, which are maintained in either an open position or a closed position, are provided on conduit system 16 to facilitate vacuuming and venting operations of filter assembly 14 and pressure regulator assembly 12. The discrete valves 19a-19e normally remain in a closed position to prohibit the passage of fluid thereacross. During a vacuum stage, however, discrete valves 19a, 19b, 19c and 19e are open and valve 19d is closed, and during a venting stage, discrete valves 19a-19d are open and valve 19e is closed. The valves 19a-19e may be automated by processor 23 or operated manually.

Although not shown, another discrete valve may be provided on sample container 11 or on the conduit between sample container 11 and regulator assembly 12 to prevent the passage of refrigerant into regulator assembly 12. Another discrete valve may also be provided on analytical instrument 20 or on conduit 17 to prevent the delivery of refrigerant into instrument 20.

Referring now to FIGS. 2-4, FIG. 2 depicts a top plan view of a heated pressure is regulator assembly 12 of FIG. 1, and FIGS. 3 and 4 depict cross-sectional views of heated pressure regulator assembly 12 of FIG. 2 taken along the lines 3-3 and 4-4, respectively. The heated pressure regulator assembly 12 includes a pressure regulator 30 that is at least partially encased within a heated sleeve 32. The pressure regulator 30 includes an inlet port 40 through which refrigerant sample is distributed into the interior of pressure regulator 30, an outlet port 42 through which the refrigerant sample is expelled from the interior of pressure regulator 30, a valve (not shown) for selectively permitting the passage of the refrigerant sample between inlet port 40 and outlet port 42, and a knob 43 for adjusting the pressure setting of pressure regulator 30. Operation of a pressure regulator is understood by those skilled in the art. A suitable pressure regulator may be offered by the Tescom Corporation of McKinney, Tex., USA.

The heated sleeve 32 is generally cylindrical and is composed of a conductive material, such as aluminum, for example. The sleeve 32 is heated by two heating elements 35. As best shown in FIG. 3, thermal contact is established between the revolved interior surface of heated sleeve 32 and the revolved exterior surface of regulator 30 at interface 36 such that thermal energy is transferred from sleeve 32 to regulator 30. The pressure regulator 30 is also composed of a conductive material such that thermal energy is transferred from the exterior surface of pressure regulator 30 to refrigerant that is contained within pressure regulator 30. The sleeve 32 at least partially encapsulates regulator 30 to evenly distribute heat across the entire revolved surface of pressure regulator 30. According to this exemplary embodiment, sleeve 32 extends around the entire circumference of pressure regulator 30, with the exception of two apertures 33 that are disposed at the lower end of sleeve 32 to accommodate inlet port 40 and outlet port 42 of regulator 30.

Two bores 34 (two shown) are formed in heated sleeve 32, wherein each bore 34 accommodates a single heating element 35. The heating elements 35 are positioned on opposing sides of heated sleeve 32 (see FIG. 2), and extend a substantial portion of the length dimension of heated sleeve 32 (see FIG. 4) to uniformly heat the surfaces of pressure regulator 30, as well as the refrigerant sample that is contained within regulator 30, to a pre-determined temperature. The heated sleeve 32 may accommodate any number of heating elements and is not limited to the embodiment shown and described herein. A thermocouple 38 is mounted to the top exterior surface of heated sleeve 32. The thermocouple 38 is configured to measure a temperature of sleeve 32 and transmit that temperature measurement to a computer processor 23 of system 10. The processor 23 controls the amount of heat emitted by heating element 35 as a function of the temperature is measurement recorded by thermocouple 38.

Figure 5:
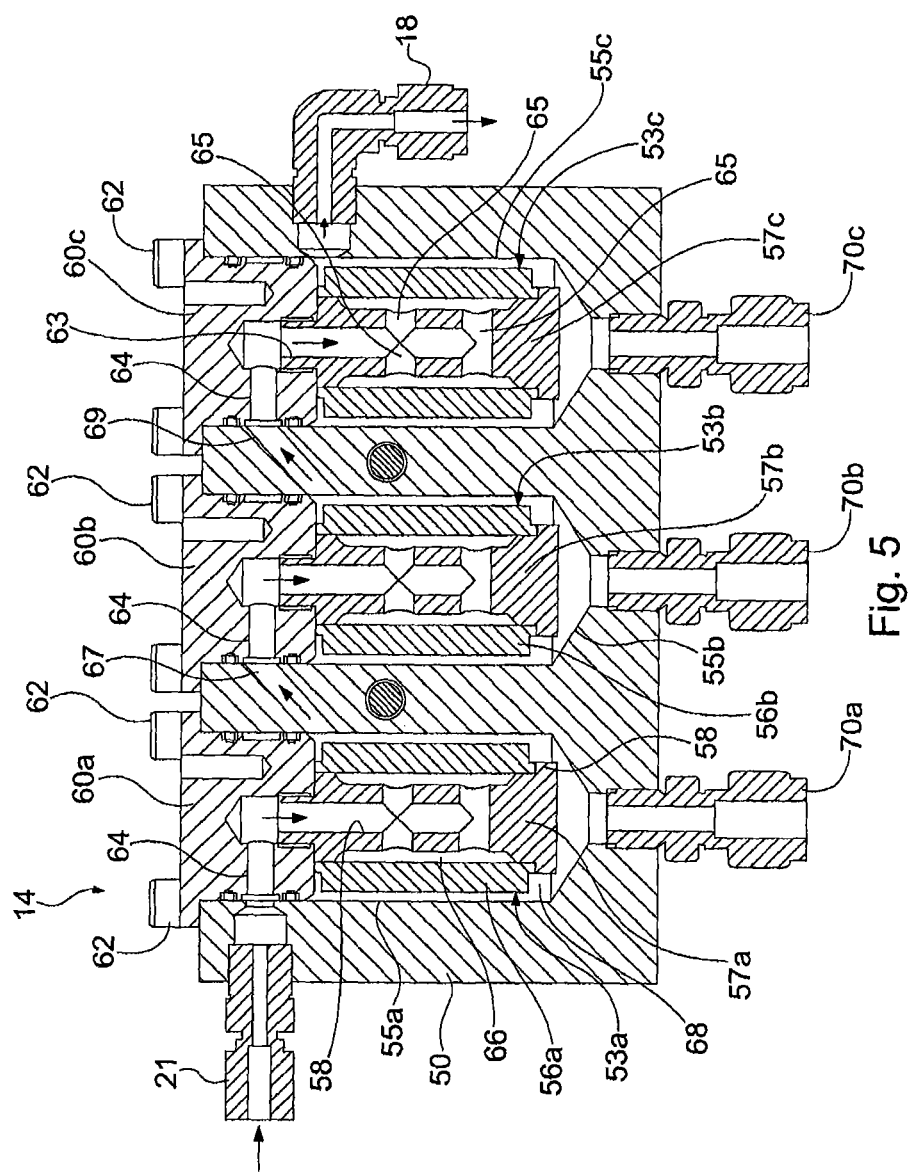
FIG. 5 is a cross-sectional view of the filter assembly of FIG. 1.

FIG. 5 depicts a cross-sectional view of filter assembly 14 of FIG. 1. The filter assembly 14 generally includes a housing 50 defining an interior fluid passageway within which three coalescing filter cartridge assemblies 53a-53c are positioned in series, an inlet port 21 coupled to housing 50 through which the heated refrigerant sample is delivered into the fluid passageway, and an outlet port 18 coupled to housing 50 through which the filtered and heated refrigerant sample is expelled. In operation, heated refrigerant sample is delivered through inlet port 21, through filter cartridge assemblies 53a-53c in sequential order and expelled through outlet port 18. In FIG. 5, the flow path of the refrigerant sample through the filter assembly 14 is indicated by arrows.

The housing 50 is a machined block of aluminum, for example. Three openings 55a-55c are defined in housing 50. One bore 67 is defined in a wall of housing 50 between openings 55a and 55b, and another bore 69 is defined in a wall of housing 50 between openings 55b and 55c. One coalescing filter cartridge assembly 53a-53c is positioned within each opening 55a-55c, respectively. Each coalescing filter cartridge assembly 53a-53c includes a coalescing filter 56a-56c mounted to a cartridge 57a-57c, respectively. An annular shoulder 59 is provided on the bottom end of each cartridge 57a-57c for mounting a coalescing filter 56a-56c, respectively. The filters 56a-56c may be adhered or merely positioned on annular shoulder 59 of cartridges 57a-57c, as shown. The coalescing filters 56a-56c have a substantially annular shape. The term 'coalescing' denotes the separation of liquid aerosols and droplets from a gas stream. The coalescing filters 56a-56c have a borosilicate glass filter element (fiber), manufactured (for example) by the Parker Hannifin Corporation.

Each cartridge 57a-57c is mounted to cover 60a-60c, and each cover 60a-60c is mounted to housing 50 by two fasteners 62, respectively. Each cover 60a-60c includes a fluid passageway 64 for delivering fluid to a coalescing filter cartridge assembly 53a-53c. More particularly, fluid passageway 64 of cover 60a fluidly connects inlet port 21 with fluid passageway 58 of cartridge 57a. The fluid passageway 64 of cover 60b fluidly connects bore 67 with fluid passageway 58 of cartridge 57b. The fluid passageway 64 of cover 60c fluidly connects bore 69 with fluid passageway 58 of cartridge 57c.

Each cartridge 57a-57c includes a substantially cylindrical body defining an interior fluid passageway 58 extending from one inlet 63 and a plurality of outlets 65 (four shown). In each coalescing filter cartridge assembly 53a-53c, an annular space 66 is defined between the exterior surface of cartridge 57a-57c and the interior surface of filter 56a-56c. In operation, heated refrigerant is directed from outlets 65 of cartridges 57a-57c into annular space 66. Another annular space 68 is defined between the exterior surface of filter 56a and the surface of opening 55a of each coalescing filter cartridge assembly 53a-53c. In operation, heated refrigerant passes through filter 56a-56c and collects in annular space 68.

An outlet fitting 70a-70c is fixed to housing 50 and is fluidly connected to the bottom end of opening 55a-55c, respectively. Each outlet fitting 70a-70c is fluidly coupled to a discrete valve 19a-19c, respectively (see FIG. 1). In an open position of one or more discrete valves 19a-19c, fluid is expelled from filter assembly 14 and is distributed through conduit system 16. Conversely, in a closed position of all three discrete valves 19a-19c, fluid is prevented from entering conduit system 16.

Referring now to the operation of refrigerant sample preparation system 10 with reference to FIGS. 1 and 5, at start-up of system 10, heating elements 35 are activated and discrete valves 19a-19e are closed. Once regulator assembly 12 reaches a pre-determined temperature, as measured by thermocouple 38, the liquid-phase oil-laden refrigerant is directed from container 11 into regulator assembly 12. Once the liquid-phase oil-laden refrigerant is heated within regulator assembly 12 to a pre-determined temperature, as measured by thermocouple 38, the refrigerant undergoes a phase change from a liquid state to a vapor state. It should be understood that heating the refrigerant increases its flow rate through system 10, which increases the speed of the refrigerant sample preparation process. Once the refrigerant reaches a vapor state, the oil-laden vapor-phase refrigerant is distributed through filter assembly 14. More particularly, the heated vapor-phase refrigerant is distributed through inlet port 21 of filter assembly 14 and into fluid passageway 64 of cover 60a. The heated refrigerant enters inlet 63 of fluid passageway 58 of cartridge 57a and exits through outlets 65 of fluid passageway 58 of cartridge 57a into annular space 66 of coalescing filter cartridge assembly 53a. The heated refrigerant flows across filter 56a and enters annular space 68 of coalescing filter cartridge assembly 53a. This represents the first pass of the refrigerant through a filter. Because discrete valve 19a is maintained in a closed position, the refrigerant is urged upwards through bore 67 of housing 50.

The once-filtered, heated refrigerant then enters fluid passageway 64 of cover 60b, travels through inlet 63 of fluid passageway 58 of cartridge 57b and exits through outlets 65 of fluid passageway 58 of cartridge 57b into annular space 66 of coalescing filter cartridge assembly 53b. The heated refrigerant flows across filter 56b and enters annular space 68 of coalescing filter cartridge assembly 53b. This represents the second pass of the refrigerant through a filter. Because discrete valve 19b is maintained in a closed position, the refrigerant is urged upwards through bore 69 of housing 50.

The twice-filtered, heated refrigerant then enters fluid passageway 64 of cover 60c, travels through inlet 63 of fluid passageway 58 of cartridge 57c and exits through outlets 65 of fluid passageway 58 of cartridge 57c into annular space 66 of coalescing filter cartridge assembly 53c. The heated refrigerant flows across filter 56c and enters annular space 68 of coalescing filter cartridge assembly 53c. This represents the third pass of the refrigerant through a filter. By the third pass, contaminants, such as oil or other lubricants, are substantially removed from the vapor-phase refrigerant. Because discrete valve 19c is maintained in a closed position, the refrigerant is urged upwards through outlet port 18 of filter assembly 14 and into conduit 17. The filtered refrigerant is then distributed into analytical instrument 20 (see FIG. 1) for analysis.

Once analysis of the refrigerant sample is complete, the system is readied for another dose of a refrigerant sample (referred to hereinafter as the second refrigerant sample or the second dose). Prior to injecting system 10 with the second dose of refrigerant, system 10 is vacuumed, flushed and vented to remove any remainder of the previous refrigerant sample. More particularly, to prepare the system for the second dose, the contents of filter assembly 14 and regulator assembly 12 are first evacuated to remove the bulk of the previous refrigerant sample. In a vacuuming procedure, discrete valves 19a-19c and 19e are opened, discrete valve 19d is closed, a discrete valve (not shown) positioned between container 11 and regulator assembly 12 is closed, and vacuum source 22 is activated. The vacuum source 22 draws a vacuum through conduit assembly 16. The contents within filter assembly 14 and regulator assembly 12 are evacuated through conduit assembly 16. The discrete valves 19a-19c may be opened either simultaneously or sequentially while vacuum source 22 is activated.

Thereafter, system 10 and analytical instrument 20 are flushed with the second dose to remove any residual of the previous refrigerant sample. To flush system 10 and analytical instrument 20, discrete valves 19a-19e are closed, and a limited quantity of the second dose is distributed through system 10 and analytical instrument 20. Thereafter, system 10 and analytical instrument 20 are vented by opening discrete valves 19a-19d. Venting system 10 and analytical instrument 20 exposes system 10 and analytical instrument 20 to atmospheric pressure to obtain a consistent volume of the second dose in analytical instrument 20. The second refrigerant dose exhausts into venting container 24. After the final venting step, the system 10 and analytical instrument 20 are now sufficiently free of the previous refrigerant sample and ready to analyze the remainder of the second dose of refrigerant. The remainder of the second dose is distributed through system 10 into analytical instrument 20. This process may be repeated continuously.

While preferred embodiments of the invention have been described herein, it will be understood that such embodiments are provided by way of example only. Numerous variations, changes and substitutions will occur to those skilled in the art without departing from the spirit of the invention. For example, the system disclosed herein is not limited to distributing refrigerant. The system may also be configured to distribute liquids, gases, flammable or non-flammable fluids, water, industrial mixtures, hydrocarbon mixtures, reactor gas mixtures or any other fluid. It is intended that the appended claims cover all such variations as fall within the spirit and scope of the invention.

What is claimed:

1. A system for preparing a refrigerant sample for analysis comprising:
   (i) a pressure regulator assembly including a pressure regulator and a means for heating a refrigerant sample contained within an interior region of the pressure regulator, said pressure regulator defining an inlet through which the refrigerant sample is delivered from a refrigerant sample container and an outlet through which the refrigerant sample is expelled;
   (ii) a filter assembly having:
      (a) a fluid passageway defined between an inlet of the filter assembly and an analyzer outlet of the filter assembly, wherein the inlet of the filter assembly is fluidly connected to the outlet of the pressure regulator to receive the vaporized refrigerant sample from the pressure regulator,
      (b) a plurality of filters for removing contaminants from the refrigerant sample that are positioned in series within the fluid passageway of the filter assembly between the inlet of the filter assembly and the analyzer outlet of the filter assembly, and
      (c) a plurality of filter outlets that are each fluidly connected with and positioned downstream of a respective filter of the plurality of filters;
   (iii) a refrigerant analysis system that is fluidly coupled to the analyzer outlet of the filter assembly for analyzing the composition of the refrigerant sample;
   (iv) a vacuum source that is coupled to each of the filter outlets of the filter assembly for drawing the refrigerant sample out of the filter assembly; and
   (v) a venting container that is fluidly coupled to each of the filter outlets of the filter assembly for receiving and storing the refrigerant sample from the filter assembly wherein the venting container is separate from the refrigerant sample container and the vacuum source.

2. The system of claim 1, wherein the pressure regulator assembly includes a thermocouple for measuring a temperature value of the refrigerant sample within the interior region of the pressure regulator.

3. The system of claim 2, further comprising a processor that communicates with the thermocouple and the means for heating to regulate the temperature of the refrigerant sample contained within the interior region of the pressure regulator.

4. The system of claim 1, wherein the pressure regulator assembly includes a metallic sleeve mounted around the pressure regulator, wherein the metallic sleeve accommodates the means for heating.

5. The system of claim 1, wherein the means for heating is a heating element.

6. The system of claim 1 wherein the filter assembly includes three filters, and the filter assembly defines a fluid flow passageway that intersects all three filters such that the refrigerant sample is delivered through all three filters.

7. A method for preparing a refrigerant sample for analysis comprising the steps of:
introducing a first dose of a refrigerant sample from a refrigerant sample container through an inlet of a pressure regulator and into an interior region of the pressure regulator;
heating the refrigerant sample within the interior region of the pressure regulator to vaporize the refrigerant sample;
sequentially distributing the vaporized refrigerant sample through a plurality of filters of a filter assembly that are fluidly connected together in series in order to remove contaminants from the refrigerant sample;
distributing the filtered and vaporized refrigerant sample from an analyzer outlet of the filter assembly and into a refrigerant analysis system for analysis;
analyzing the filtered and vaporized refrigerant sample using the refrigerant analysis system;
drawing the filtered, vaporized and analyzed refrigerant sample under vacuum pressure through separate filter outlets of the filter assembly that are each fluidly connected with and positioned downstream of a respective filter of the plurality of filters; and
distributing a second dose of the refrigerant sample from the refrigerant sample container and into the pressure regulator, and then through the plurality of filters and then into a venting container that is separate from the refrigerant sample container and the vacuum source.

8. The method of claim 7 further comprising the step of measuring a temperature of either the pressure regulator or the refrigerant sample within the interior region of the pressure regulator.

9. The method of claim 8 further comprising the step of regulating a level of heat applied to the refrigerant sample as a function of the temperature measurement.

* * * * *